United States Patent [19]

Bommier et al.

[11] Patent Number: 4,898,646

[45] Date of Patent: Feb. 6, 1990

[54] PROCESS FOR IDENTIFYING AL ALLOYS BY ELECTROCHEMICAL MEANS

[75] Inventors: Christophe Bommier, Moirans; Philippe Gimenez, Grenoble; Jean-Claude Kucza, St. Etienne de Crossey; Jacques Rabiet, Goncelin, all of France

[73] Assignee: Pechiney, Paris, France

[21] Appl. No.: 346,532

[22] Filed: May 2, 1989

[30] Foreign Application Priority Data

May 3, 1988 [FR] France ................. 88 06431

[51] Int. Cl.$^4$ ........................... G01N 27/46
[52] U.S. Cl. ........................... 204/1 T; 204/58; 204/434
[58] Field of Search ............ 204/1 T, 434, 58

[56] References Cited

U.S. PATENT DOCUMENTS 2,531,747 11/1950 Stearn ................. 204/58 X
3,428,532 2/1969 Banks ................. 204/1 T

OTHER PUBLICATIONS

Joseph V. Petrocelli et al., The Electrochemical Soc., Preprint 85-6, pp. 51-70 (1944).

N. A. Gordienko, Theor. & Exp. Chem. (U.S.A.), vol. 7, No. 5, pp. 581-584, (Sep.-Oct. 1971).

Primary Examiner—G. L. Kaplan
Attorney, Agent, or Firm—Dennison, Meserole, Pollack & Scheiner

[57] ABSTRACT

This invention relates to a process for identifying the external surface or surfaces of an Al alloy of a homogeneous or composite material by electrochemical means. This method involves forming an anodic layer, in situ, on the products to be identified, by electrolysis under predetermined conditions and following or plotting the development of the voltage U at the terminals of the electrolyzer as a function of time t during an intentiostatic test. The shape and relative position of curves U=f(t), thus obtained, allows the various alloys tested to be identified from a comparison of the derived curve from a curve U=f(t) derived from a known sample. The present method has advantages over the earlier methods of marking in that it provides: non-destructive method employable in situ on products which may have large dimensions (coils, plates, sheets, etc.); almost instantaneous identification; high reliability; and is simple and economic to use.

12 Claims, 5 Drawing Sheets

PROCESS FOR IDENTIFYING AL ALLOYS BY ELECTROCHEMICAL MEANS

BRIEF SUMMARY OF THE INVENTION

The invention relates to a process for identifying the external, Al alloy surface or surfaces of a homogeneous or composite material by electrochemical means.

The invention is based on the practical problems encountered by manufacturers as well as by customers in identifying, throughout the production range and in a rapid and non-destructive manner, the nature of an Al-based homogeneous material or of an Al-based clad or plated composite of the type found, for example, in the production of brazed heat exchangers.

This identification applies to all groups of Al alloys. Plated composites are frequently made up according to the Aluminium Association specifications from a core of 3003 plated on a surface of a different alloy such as 4045, 4104 or 4343, or even a 3003 alloy plated on a surface by a 4343 alloy and by a 7072 alloy on the other surface.

The method according to the invention involves forming an anodic layer, in situ, on the product to be identified, by electrolysis under predetermined conditions and following the development of, e.g. plotting the curve of, the voltage U at the terminals of the electrolyzer as a function of the time t during an intensiostatic test. As mentioned below, the shape and relative position of the curves $U=f(t)$ thus obtained allow the various alloys tested to be identified by virtue of the fact that curves have been plotted from samples of known numerically designated Al alloys.

More specifically, anodization carried out in the following manner:
intensity: constant between 0.1 mA/cm$^2$ and 100 mA/cm$^2$ of anode surface
temperature: constant to within $\pm 2°$ C. between 0° and 100° C.
electrolyte: may be selected from solutions of ammonium, sodium or potassium tartrate, citrate, borate, tetraborate or adipate or of a mixture of these salts, the concentration of which is between 1 g/l and saturation.
the cathode being formed by a 3003 or 1199 alloy
the duration of the test is generally less than 7 minutes.

The invention will be understood better by means of the following examples, illustrated by FIGS. 1 to 4.

DETAILED DESCRIPTION OF THE INVENTION

Figure 1:
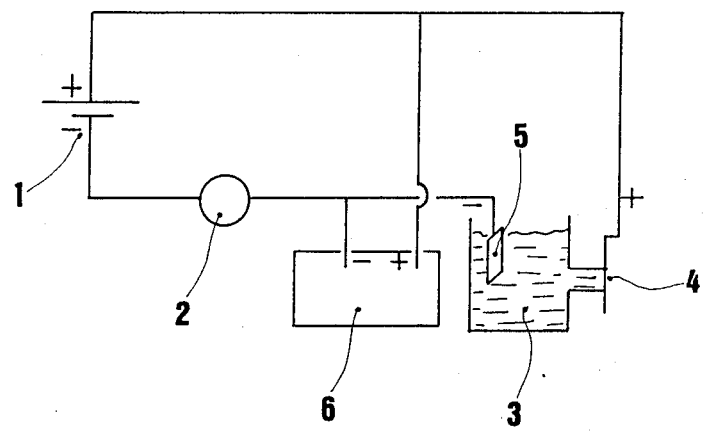
FIG. 1 shows the electrical diagram of the device used.

The electrical assembly (FIG. 1) comprises a direct current generator 1, for example of 12 V - 20 mA, connected in series with an intensiostat, or ammeter, 2 and the electrolytic cell 3, of which the anode is the sample to be analyzed 4 and the cathode 5 is of 3003. A voltage indicating and/or recording device 6 $U=f(t)$ is branched off at the terminals of the electrolyzer.

Figure 2:
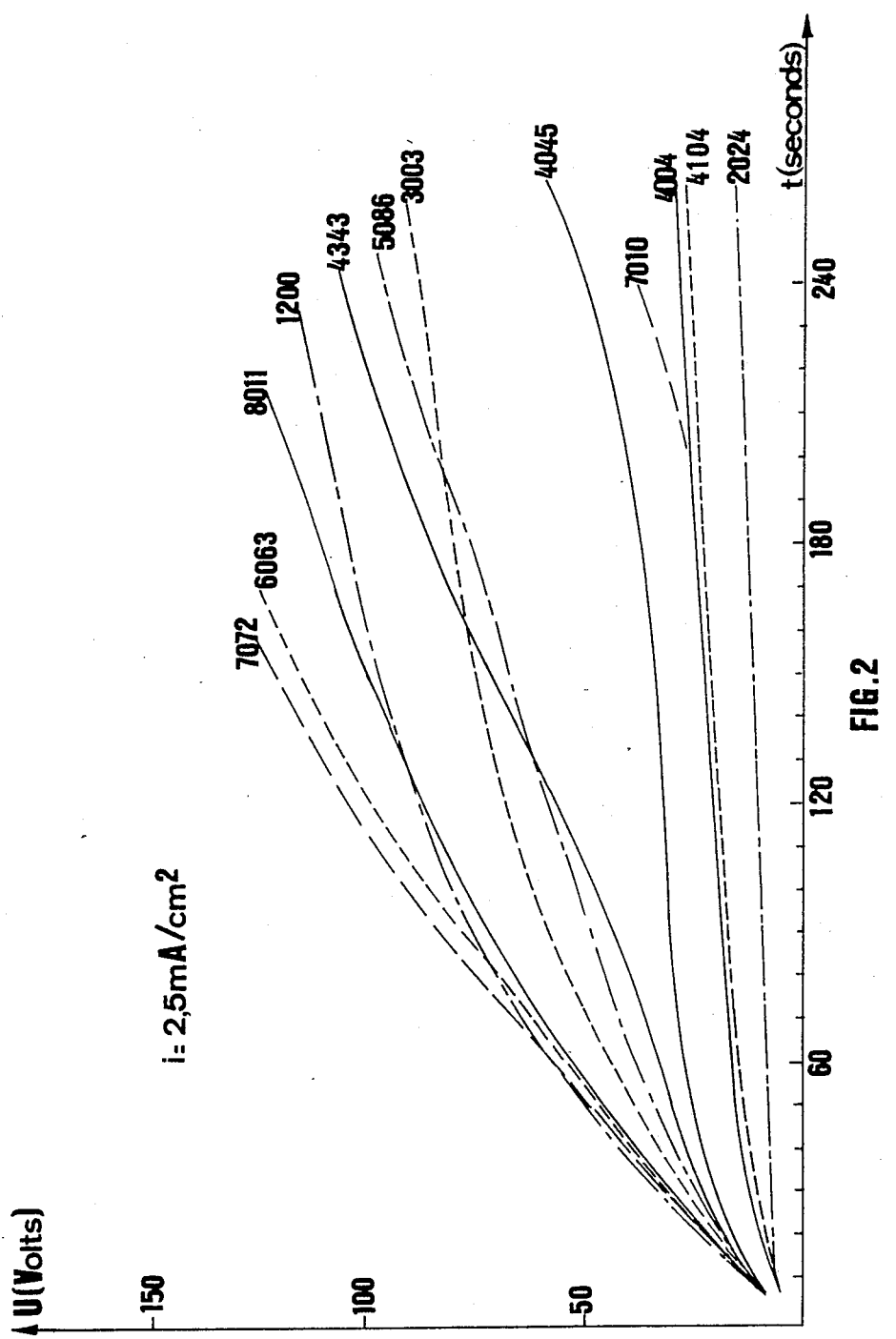
FIG. 2 shows the mean curves $U=f(t)$ for various alloys under the conditions of Example I (i=2.5 mA/cm$^2$.
Figure 4:
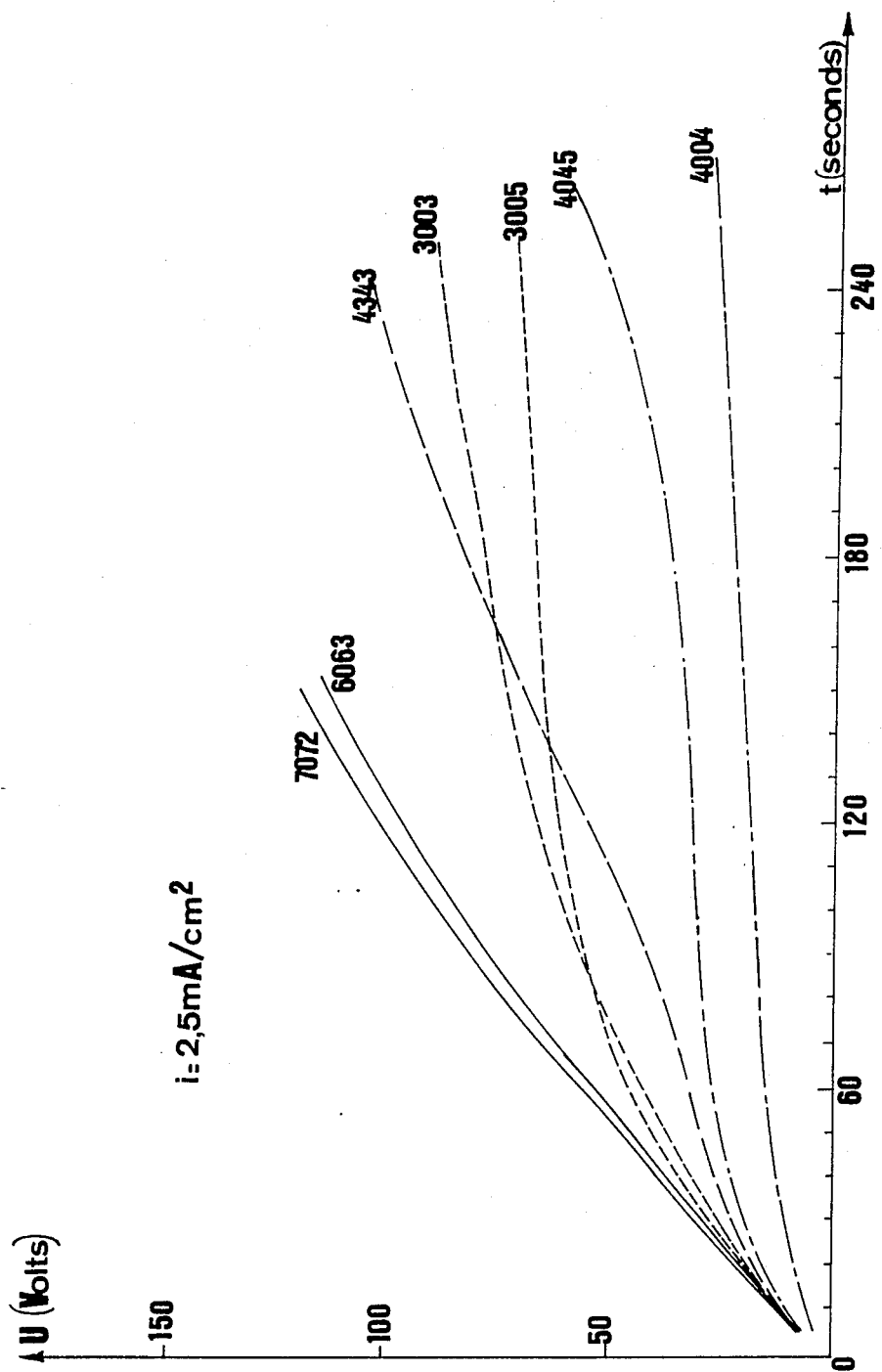
FIG. 4 shows the mean curves $U=f(t)$ for i=2.5 mA/cm$^2$ in the case of plated alloys.
Figure 5:
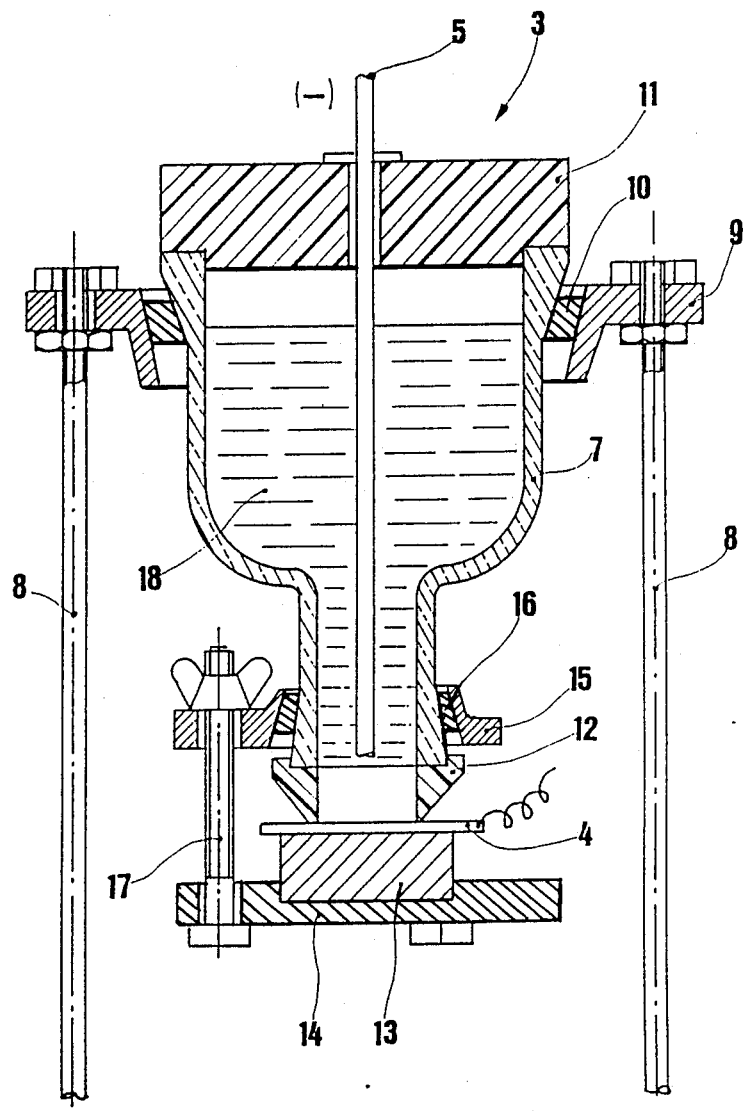
FIG. 5 shows schematically an axial section through the electrolyzer used.

The curves in FIGS. 2 and 4 were established with the cell shown in FIG. 5 in a solution containing 30 g/l of ammonium tartrate, kept at 20° C.$\pm 2°$ C. and at an anode current density of 2.5 mA/cm$^2$.

Figure 3:
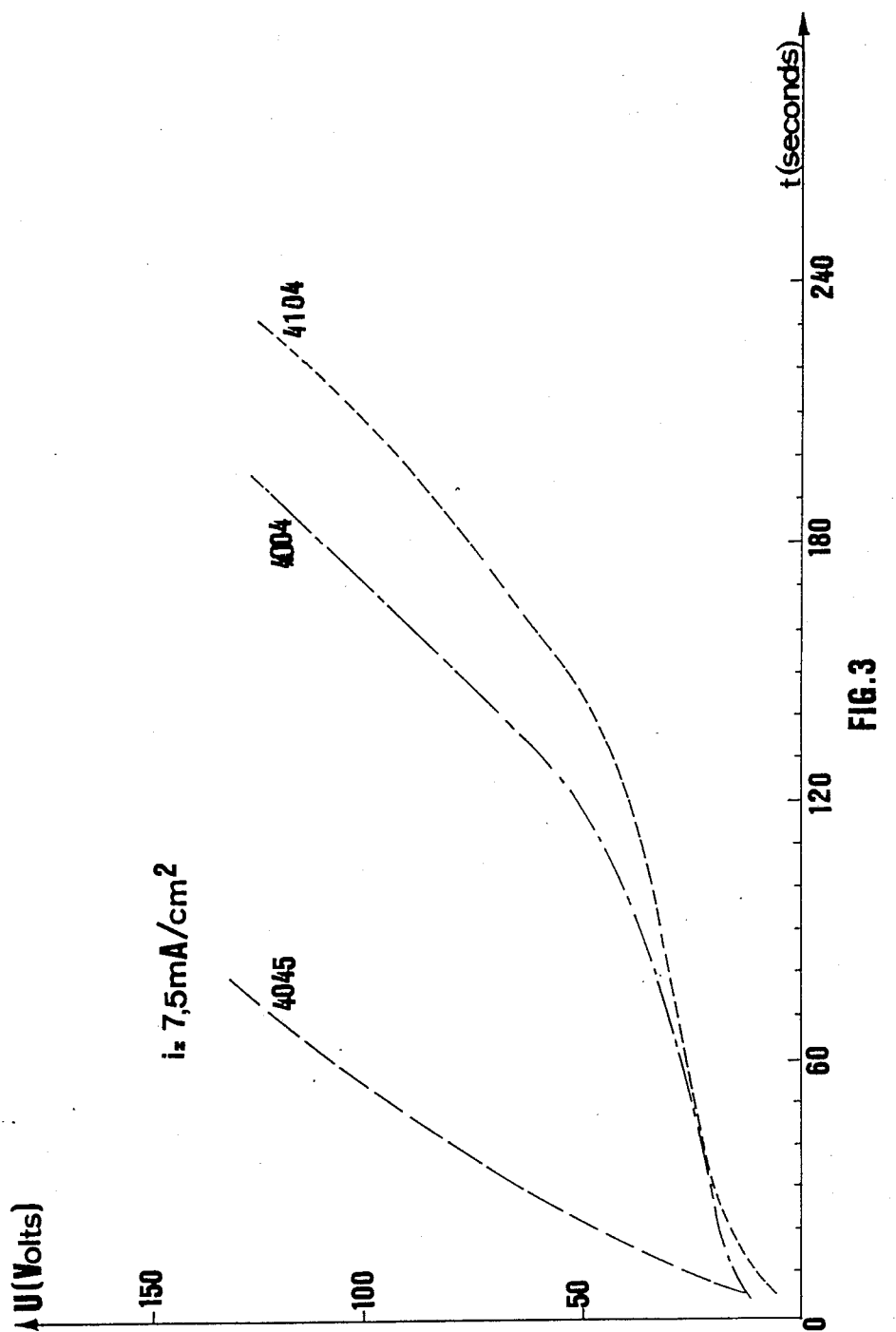
FIG. 3 shows the mean curves $U=f(t)$ for the 4000 alloys with a current density of 7.5 mA/cm$^2$.

The curves in FIG. 3 were established under the same conditions but with a current density of 7.5 mA/cm$^2$.

It can be observed that the curves $U=f(t)$ of the 4004 and 4014, which virtually coincide when i=2.5 mA/cm$^2$ (FIG. 2), differ markedly when i=7.5 mA/cm$^2$ (FIG. 3).

It can be seen in FIG. 2 that the greatest sensitivity is obtained for test times ranging from 80 to 120 sec., the optimum being about 100 seconds for a current density of 2.5 mA/cm$^2$.

If the discrimination between alloys is inadequate at a certain current density, the test is repeated with a higher current density.

The electrolyzer used is shown in FIG. 5. It comprises an electrolytic cell 7 of PYREX supported by an underframe 8, a supporting flange 9 and a seal 10. It is formed at its top by a PLEXIGLASS cover 11 which is traversed by the cathode 5.

The sample 4, a strip in this case, is fixed to the bottom of the electrolyzer 3 by a Teflon seal 12 and a screw 17 type gripping system 13, 14, 15, 16. The electrolyzer is filled with the electrolyte 18.

The electrolyzer used can be of a different type from the one shown in FIG. 5. In particular, it can be of the "buffer" type, in which the electrolyte is supported by a porous medium (felt, sintered glass, etc.) with direct manual application on to the sample to be analyzed.

The process according to the invention has the following advantages over the marking methods of the prior art:
non-destructive method employable in situ on products which may have large dimensions (coils, plates, sheets, etc.);
almost instantaneous identification;
high reliability; and
simple and economic to use.

We claim:

1. Method of determining the nature of Al alloys of unknown designation comprising the steps of: subjecting a sample of an Al alloy to anodization to determine the shape and relative position of the curve $U=f(t)$ during intensiostatic operation, U being the voltage at the terminals of an electrolyzer and t the time, of which the analyzed sample constitutes the anode, the cathode being of 3003 or 1199; and making a comparison of the determined curve with a curve $U=f(t)$ derived from an Al alloy of known designation to generally establish coincidence of the two curves.

2. Method according to claim 1, characterized in that the density of anodic current (d) in the electrolyzer is between 0.1 and 100 mA/cm$^2$.

3. Method according to claim 1 or 2, characterized in that the electrolyte of the electrolyzer is a solution containing 1 g/liter to saturation, of a salt selected from the group consisting of salts based on ammonium, sodium or potassium tartrate, citrate, borate, tetraborate or adipate, and mixtures thereof.

4. Method according to claim 1 or 2, characterized in that the temperature in the electrolyzer is between 0° and 100° C. and is kept constant within $\pm 2°$ C.

5. Method according to claim 1 or 2, characterized in that the duration of the test is between 80 and 120 seconds when $d=2.5$ mA/cm$^2$.

6. Method according to claim 1 or 2, characterized in that preliminary determination of the curve $U=f(t)$ is carried out at low anodic current density, then final determination of the curve $U=f(t)$ at high anodic current density.

7. Method of determining and identifying the alloy designation of an Al alloy comprising the steps of:
(a) empirically determining by means of anodization at a predetermined current density and temperature in an electrolyzer of a known designated Al alloy a voltage-time curve $U=f(t)$ for the known numerically designated Al alloy;
(b) subjecting a sample of an Al alloy of unknown designation to anodization under essentially the same conditions as in (a) and deriving a curve $U=f(t)$ with respect thereto; and
(c) comparing the curves $U=f(t)$ of (a) and (b) to determine essential coincidence of the two curves to thus identify the unknown Al alloy as being the same as the known alloy, and wherein $U=$ voltage across an anodization apparatus used, and
$f(t)=$ function of time.

8. Method according to claim 7, characterized in that the density of anodic current (d) in the electrolyzer is between 0.1 and 100 mA/cm$^2$.

9. Method according to claim 7, characterized in that the electrolyte of the electrolyzer is a solution containing 1 g/liter to saturation, of a salt selected from the group consisting of salts based on ammonium, sodium or potassium tartrate, citrate, borate, tetraborate or adipate, and mixtures thereof.

10. Method according to claim 7, characterized in that the temperature in the electrolyzer is between 0° and 100° C. and is kept constant within ±2° C.

11. Method according to claim 7, characterized in that the duration of the test is between 80 and 120 seconds when $d=2.5$ mA/cm$^2$.

12. Method according to claim 7, characterized in that preliminary determination of the curve $U=f(t)$ is carried out at low anodic current density, then final determination of the curve $U=f(t)$ at high anodic current density.

* * * * *